United States Patent

Onozawa et al.

(10) Patent No.: US 10,646,127 B2
(45) Date of Patent: May 12, 2020

(54) BLOOD FLOW ANALYSIS DEVICE, METHOD, AND PROGRAM

(71) Applicant: FUJIFILM Corporation, Tokyo (JP)

(72) Inventors: Sho Onozawa, Tokyo (JP); Takeshi Unemura, Tokyo (JP); Hirotaka Ito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 166 days.

(21) Appl. No.: 15/904,688

(22) Filed: Feb. 26, 2018

(65) Prior Publication Data

US 2018/0242856 A1 Aug. 30, 2018

(30) Foreign Application Priority Data

Feb. 28, 2017 (JP) ................................ 2017-037061

(51) Int. Cl.
*A61B 5/026* (2006.01)
*A61B 6/00* (2006.01)
(Continued)

(52) U.S. Cl.
CPC ................ *A61B 5/026* (2013.01); *A61B 6/03* (2013.01); *A61B 6/504* (2013.01); *A61B 6/5217* (2013.01);
(Continued)

(58) Field of Classification Search
CPC ......... A61B 5/026; A61B 6/504; A61B 34/10; A61B 6/507; A61B 8/06; G16H 50/50;
(Continued)

(56) References Cited

U.S. PATENT DOCUMENTS

| 9,984,465 | B1 * | 5/2018 | Ma | .......................... A61B 5/026 |
| 2010/0056931 | A1 * | 3/2010 | Soffer | ................ A61B 5/02028 600/486 |

(Continued)

FOREIGN PATENT DOCUMENTS

| JP | 2015-171486 A | 10/2015 |
| JP | 2016-500548 A | 1/2016 |

(Continued)

OTHER PUBLICATIONS

Sato, et al., "Three-dimensional multi-scale line filter for segmentation and visualization of curvilinear structures in medical images. ", Medical Image Analysis, Jun. 1998, vol. 2, No. 2, pp. 143-168.

*Primary Examiner* — Jingge Wu
(74) *Attorney, Agent, or Firm* — Birch, Stewart, Kolasch & Birch, LLP (57) ABSTRACT

A blood flow analysis device includes a blood vessel region extraction unit that extracts a blood vessel region from a three-dimensional medical image of a subject including a blood vessel, and a blood flow simulation unit that obtains a line resistance by multiplying a resistance value corresponding to a branch blood vessel branching out of the blood vessel region by a surface area of each of preset sections into which the blood vessel region is divided in an extension direction, generates a vascular network model by applying the line resistance to each node of a surface of the blood vessel region, and performs simulation of a blood flow by using the vascular network model.

11 Claims, 5 Drawing Sheets

(51) Int. Cl.
  *A61B 6/03* (2006.01)
  *G16H 30/40* (2018.01)
  *G16H 50/50* (2018.01)
(52) U.S. Cl.
  CPC ............ *G16H 30/40* (2018.01); *G16H 50/50* (2018.01); *A61B 6/5229* (2013.01); *A61B 2576/023* (2013.01); *G06T 2207/30104* (2013.01)
(58) Field of Classification Search
  CPC ... G16H 30/40; G06F 17/5009; G06F 19/321; G06T 17/00; G06T 19/00; G06T 2210/24; G06T 2210/41; G06T 2207/30104
  See application file for complete search history.

(56) References Cited

U.S. PATENT DOCUMENTS

| | | | | |
|---|---|---|---|---|
| 2011/0103665 | A1* | 5/2011 | Gulsun | G06T 7/248 382/131 |
| 2014/0200867 | A1* | 7/2014 | Lavi | G06T 7/0012 703/2 |
| 2014/0316758 | A1* | 10/2014 | Yagi | G16H 50/50 703/9 |
| 2015/0038860 | A1 | 2/2015 | Fonte et al. | |
| 2015/0216425 | A1* | 8/2015 | Gladshtein | A61B 3/1233 600/431 |
| 2015/0282765 | A1 | 10/2015 | Goshen et al. | |
| 2015/0335304 | A1* | 11/2015 | Lavi | G06F 19/321 600/407 |
| 2015/0339847 | A1* | 11/2015 | Benishti | G16H 50/30 382/131 |
| 2016/0367154 | A1* | 12/2016 | Gladshtein | F16L 33/30 |
| 2017/0095221 | A1* | 4/2017 | Kato | G16H 50/30 |
| 2017/0323587 | A1* | 11/2017 | Yagi | G06T 7/11 |

FOREIGN PATENT DOCUMENTS

| | | |
|---|---|---|
| JP | 2016-509501 A | 3/2016 |
| JP | 2016-528975 A | 9/2016 |

* cited by examiner

BLOOD FLOW ANALYSIS DEVICE, METHOD, AND PROGRAM

CROSS-REFERENCE TO RELATED APPLICATION

This application claims priority from Japanese Patent Application No. 2017-037061, filed on Feb. 28, 2017, the disclosure of which is incorporated by reference herein in its entirety.

BACKGROUND

Field of the Invention

The present invention relates to a blood flow analysis device, method, and program for performing simulation of a blood flow flowing through a blood vessel region by using the blood vessel region extracted from a three-dimensional medical image.

The Related Art

A fractional flow reserve (FFR) is measured for a stenotic lesion occurring in coronary artery as indexes for ischemic determination and determination of application of percutaneous coronary intervention (PCI).

In recent years, a technique has been proposed in which a blood flow in coronary artery is analyzed with computational fluid dynamics (CFD) by using volume data of the coronary artery, and thus an FFR is obtained in a non-invasive manner (for example, JP2016-528975T).

JP2015-171486A, JP2016-500548A, and JP2016-509501T have also proposed techniques of performing blood flow simulation by using image data of a blood vessel.

Here, the present inventors have found through examination that an analysis result of an FFR of a stenotic part is greatly influenced by a flow resistance value on a downstream side of the stenotic part. It has also been found that, in order to obtain an FFR with required accuracy, it is important to calculate a resistance value by modeling a peripheral vascular network of an invisible region exceeding a resolution of volume data according to any method, and to perform blood flow analysis. Here, the present inventors have replaced a blood vessel on the downstream side of the stenotic part with a blood vessel model which is generated by using a fractal model or the like, and tried analysis using the CFD.

However, in a case where a blood vessel is replaced with the blood vessel model as mentioned above, it has been found that there is a difference between analysis results depending on a position on the downstream side of the stenotic part at which the prior blood vessel is modeled. Specifically, in a case where the prior blood vessel is modeled at any position on the downstream side of the stenotic part, a diameter of the blood vessel varies due to a slight error of the position on the downstream side. Therefore, it has been found that, if a blood vessel model corresponding to the diameter is generated, there is a difference between blood flow analysis results due to a difference between resistance values of the blood vessel model, and thus it is hard to measure an FFR with high accuracy.

Actually, since blood vessels branch out of an end of the coronary artery, and fine blood vessels of a fine artery level or less also directly branch out of a surface of the coronary artery, and become capillary vessels through further repeated branching, so as to get into cardiac muscles, it is hard to perform highly accurate blood flow analysis as long as the CFD is performed without taking into consideration such fine blood vessels.

An object of the present invention is to provide a blood flow analysis device, method, and program capable of analyzing a blood flow flowing through a blood vessel with high accuracy, and measuring an FFR or the like with high accuracy, in light of the circumstances.

SUMMARY

According to the present invention, there is provided a blood flow analysis device including a blood vessel region extraction unit that extracts a blood vessel region from a three-dimensional medical image of a subject including a blood vessel; and a blood flow simulation unit that obtains a line resistance by multiplying a resistance value corresponding to a branch blood vessel branching out of the blood vessel region by a surface area of each of preset sections into which the blood vessel region is divided in an extension direction, generates a vascular network model by applying the line resistance to each node of a surface of the blood vessel region, and performs simulation of a blood flow by using the vascular network model.

In the blood flow analysis device according to the present invention, the blood flow simulation unit may change the resistance value corresponding to the branch blood vessel according to a size of the blood vessel region in which each node is disposed.

In the blood flow analysis device according to the present invention, the blood flow simulation unit may change the surface area according to a size of the blood vessel region in which each node is disposed.

In the blood flow analysis device according to the present invention, the blood flow simulation unit may connect a peripheral vascular model which does not appear as the blood vessel region on the three-dimensional medical image to an end of the blood vessel region, and apply a line resistance calculated on the basis of the peripheral vascular model to the end of the blood vessel region, so as to generate the vascular network model.

In the blood flow analysis device according to the present invention, the blood vessel region extraction unit may extract the blood vessel region including coronary artery from the three-dimensional medical image of a heart as the subject.

The blood flow analysis device according to the present invention may further include a display control unit that displays an image indicating the blood flow on a display unit on the basis of a simulation result of the blood flow.

In the blood flow analysis device according to the present invention, the display control unit may display the image indicating the blood flow to overlap the blood vessel region.

In the blood flow analysis device according to the present invention, the display control unit may display the image indicating the blood flow in colors.

According to the present invention, there is provided a blood flow analysis method including extracting a blood vessel region from a three-dimensional medical image of a subject including a blood vessel; and generating a vascular network model by applying a line resistance obtained by multiplying a resistance value corresponding to a branch blood vessel branching out of the blood vessel region by a surface area of a preset region including each point, to each point of a surface of the blood vessel region, and performing simulation of a blood flow by using the vascular network model.

According to the present invention, there is provided a blood flow analysis program causing a computer to function as a blood vessel region extraction unit that extracts a blood vessel region from a three-dimensional medical image of a subject including a blood vessel; and a blood flow simulation unit that generates a vascular network model by applying a line resistance obtained by multiplying a resistance value corresponding to a branch blood vessel branching out of the blood vessel region by a surface area of a preset region including each point, to each node of a surface of the blood vessel region, and performs simulation of a blood flow by using the vascular network model.

According to the present invention, there is provided another blood flow analysis device including a memory that stores a command to be executed in a computer; and a processor that is configured to execute a stored command, in which the processor performs a process of extracting a blood vessel region from a three-dimensional medical image of a subject including a blood vessel, and a process of obtaining a line resistance obtained by multiplying a resistance value corresponding to a branch blood vessel branching out of the blood vessel region by a surface area of each of preset sections into which the blood vessel region is divided in an extension direction, generating a vascular network model by applying the line resistance to each node of a surface of the blood vessel region, and performing simulation of a blood flow by using the vascular network model.

According to the blood flow analysis device, method, and program of the present invention, a blood vessel region is extracted from a three-dimensional medical image of a subject including a blood vessel, a line resistance is obtained by multiplying a resistance value corresponding to a branch blood vessel branching out of the blood vessel region by a surface area of each of preset sections into which the blood vessel region is divided in an extension direction, a vascular network model is generated by applying the line resistance to each node of a surface of the blood vessel region, and simulation of a blood flow by using the vascular network model is performed. In other words, since the line resistance is calculated by taking into consideration a fine blood vessel of the fine artery level or less, and is applied to each node of the surface of the blood vessel region, blood flow simulation can be performed by using a vascular network model obtained by modeling even the fine blood vessel of the fine artery level or less. Consequently, a blood flow flowing through a blood vessel can be analyzed with high accuracy, and thus an FFR or the like can be measured with high accuracy.

DETAILED DESCRIPTION

Figure 1:
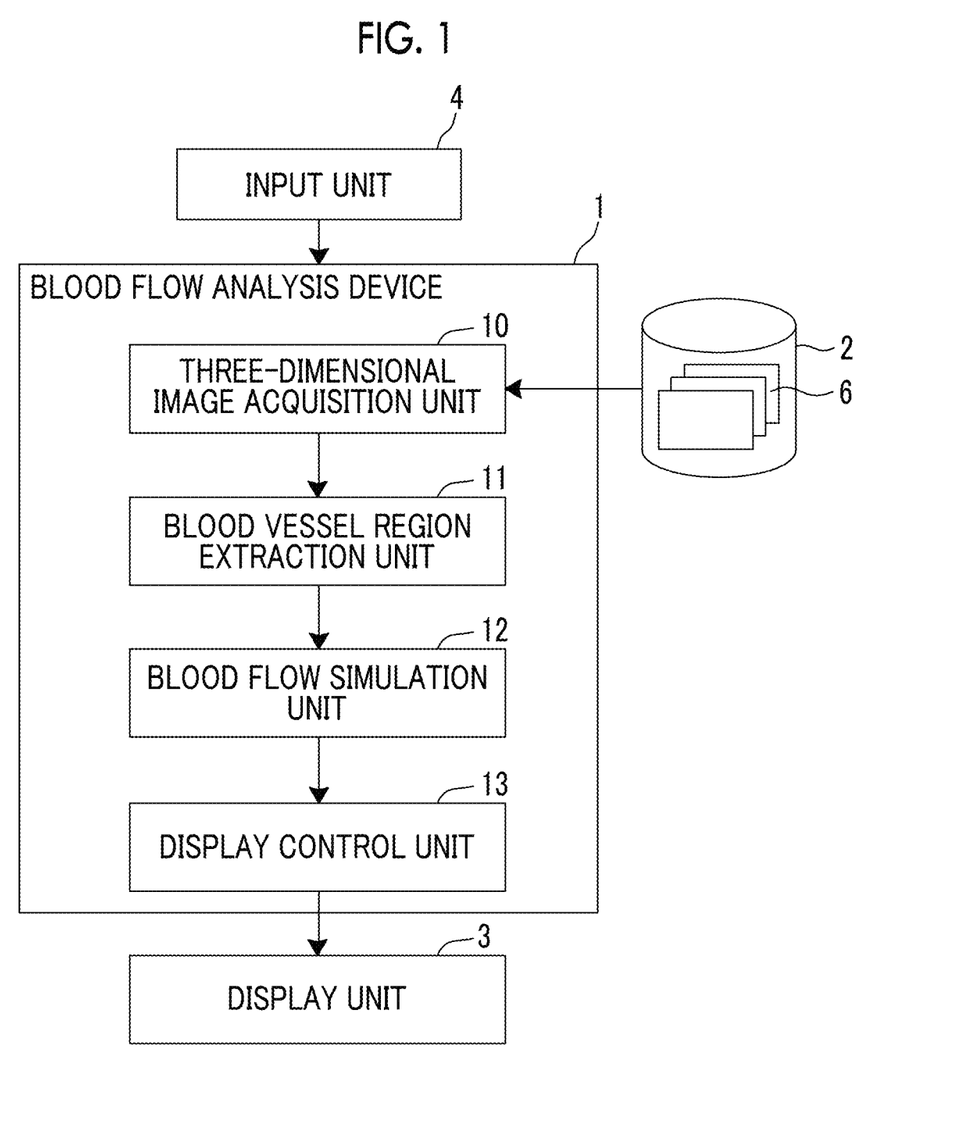
FIG. 1 is a block diagram illustrating a schematic configuration of a blood flow analysis system using an embodiment of a blood flow analysis device of the present invention.

Hereinafter, with reference to the drawings, a description will be made of a blood flow analysis system using an embodiment of a blood flow analysis device of the present invention. FIG. 1 is a block diagram illustrating a schematic configuration of a blood flow analysis system of the present embodiment.

The blood flow analysis system of the present embodiment includes, specifically, a blood flow analysis device 1, a medical image storage server 2, a display unit 3, and an input unit 4 as illustrated in FIG. 1.

The blood flow analysis device 1 is obtained by installing a blood flow analysis program of the present embodiment in a computer.

The blood flow analysis device 1 includes a central processing unit (CPU), a semiconductor memory, and a storage device such as a hard disk or a solid state drive (SSD). The blood flow analysis program of the present embodiment is installed in the storage device, and the central processing unit executes the blood flow analysis program such that a three-dimensional image acquisition unit 10, a blood vessel region extraction unit 11, a blood flow simulation unit 12, and a display control unit 13 illustrated in FIG. 1 are operated.

The blood flow analysis program is recorded on a recording medium such as a digital versatile disc (DVD) and a compact disc read only memory (CD-ROM) and is distributed, and is installed in a computer from the recording medium. The blood flow analysis program is stored in a storage device of a server computer connected to a network or a network storage in a state in which the program can be accessed from the outside. The blood flow analysis program is downloaded to and installed in the computer in response to a request from the outside.

The three-dimensional image acquisition unit 10 acquires a three-dimensional medical image 6 of a patient captured in advance. The three-dimensional medical image 6 is volume data obtained through imaging using, for example, a computed tomography (CT) device or a magnetic resonance imaging (MRI) device. In the present embodiment, a description will be made of a case where the three-dimensional medical image 6 of a heart (corresponding to a subject of the present invention) of the patient is acquired, but this is only an example, and images of other organs such as a lung, a liver, and a head may be acquired.

The three-dimensional medical image 6 is reserved in the medical image storage server 2 along with identification information of the patient, and the three-dimensional image acquisition unit 10 reads the three-dimensional medical image 6 having identification information from the medical image storage server 2 and temporarily stores the three-dimensional medical image 6 on the basis of the identification information of the patient which is input by a user by using the input unit 4 or the like.

The blood vessel region extraction unit 11 extracts a blood vessel region from the three-dimensional medical image 6. Specifically, the blood vessel region extraction unit 11 of the present embodiment extracts a region of coronary artery from the three-dimensional medical image 6 of the heart as the blood vessel region. The blood vessel region extraction unit 11 performs, for example, multi-resolution transform on the three-dimensional medical image 6 of the heart, so as to perform eigenvalue analysis of a Hesse matrix on images with respective resolutions, and extracts a region of coronary artery as an aggregate of line structures (blood vessels) with various sizes in the heart region by integrating analysis results of the images with the respective resolutions (for example, refer to Y Sato, et al., "Three-dimensional multi-scale line filter for segmentation and visualization of curvilinear structures in medical images.", Medical Image Analysis, June, 1998, Vol. 2, No. 2, p.p. 143 to 168). Central points of the respective extracted line structures may be further connected to each other by using a minimum spanning tree algorithm or the like, so that tree structure data indicating the coronary artery is generated, a section orthogonal to a core line may be obtained at each point (each node of the tree structure data) on the core line connecting the central points of the extracted coronary artery, a contour of the coronary artery may be recognized by using a well-known segmentation method such as a graph cut method in each section, and a region of the coronary artery may be extracted by correlating information indicating the contour with each node of the tree structure data.

A method of extracting a region of coronary artery is not limited to the method, and other well-known methods such as a region expansion method may be used.

The blood flow simulation unit 12 simulates a blood flow flowing through the blood vessel region through a calculation process on the basis of the blood vessel region (the region of the coronary artery) extracted by the blood vessel region extraction unit 11.

Here, in the present embodiment, as described above, the region of the coronary artery is extracted from the three-dimensional medical image 6, but a blood vessel region which can be extracted at a high resolution is only a thick epicardial coronary artery region due to a limit of a resolution of the three-dimensional medical image 6. However, actually, since blood vessels of a fine artery level or less also directly branch out of a surface of the coronary artery, and become capillary vessels through further repeated branching, so as to get into cardiac muscles, it is hard to perform highly accurate blood flow analysis as long as the CFD is performed without taking into consideration such fine blood vessels. Therefore, if blood flow simulation is performed without taking into consideration such fine blood vessels, it is hard to perform highly accurate blood flow analysis.

Therefore, the blood flow simulation unit 12 of the present embodiment generates a blood flow network model in which a fine blood vessel of the fine artery level or less is also taken into consideration, and performs blood flow simulation by using the vascular network model. Hereinafter, a description will be made of a vascular network model generated by the blood flow simulation unit 12 of the present embodiment.

Figure 2:
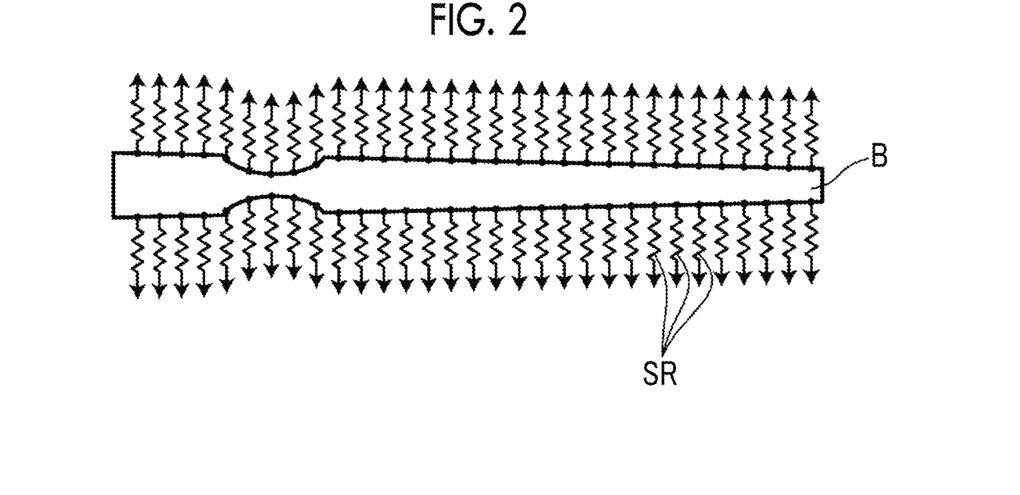
FIG. 2 is a schematic diagram illustrating an example of a vascular network model.

FIG. 2 is a diagram schematically illustrating a vascular network model generated in the present embodiment. In FIG. 2, for better understanding, a blood vessel region B extracted from the three-dimensional medical image 6 is illustrated to be linear. A thinned portion of the blood vessel region B illustrated in FIG. 2 indicates a stenotic lesion.

The blood flow simulation unit 12 applies a line resistance SR to each point on a surface of the blood vessel region B extracted from the three-dimensional medical image 6 so as to generate a vascular network model, and performs blood flow simulation by using the vascular network model as illustrated in FIG. 2. The line resistance SR is a value obtained by multiplying a branch resistance R (corresponding to a resistance value corresponding to a branch blood vessel of the present invention) corresponding to a branch blood vessel of the fine artery level or less, branching out of the blood vessel region B, by a surface area S of each of preset sections into which the blood vessel region B is divided in an extension direction. Hereinafter, the preset section will be referred to as a segment.

Specifically, the blood flow simulation unit 12 generates a surface model formed of a polyhedron on the basis of the blood vessel region extracted from the three-dimensional medical image 6. The surface model is defined by a mesh structure in which a plurality of patches such as polygonal or parametric curved surfaces are sewn up together. As a method of generating the mesh structure, for example, a well-known method such as a Deloney division method may be used.

The blood flow simulation unit 12 allocates the line resistance SR to each node of the surface model of the blood vessel region. The node is the vertex of the patch forming the surface model. The line resistances SR are preferably allocated to all nodes, but may not be allocated to some of the nodes.

Figure 3:
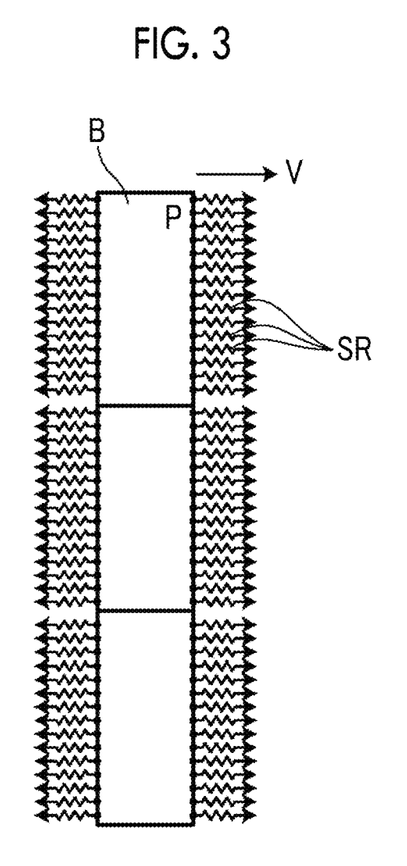
FIG. 3 is a diagram for explaining blood flow analysis using the vascular network model.

As described above, the blood flow simulation unit 12 performs blood flow simulation by performing blood flow analysis based on computational fluid dynamics (CFD) by using the vascular network model formed as described above. Specifically, as described above, the line resistance SR is applied to each node of the blood vessel region B, blood flow analysis based on the CFD is performed such that a pressure P of each node is obtained as illustrated in FIG. 3, and a surface outflow velocity V at each node is obtained by dividing the pressure P by the line resistance SR as shown in the following equation. In FIG. 3, the blood vessel region B is schematically illustrated to be linear, and a section divided as a rectangular shape illustrated in FIG. 3 indicates a segment set at a predetermined node.

$$V=P/(SR)$$

Blood flow analysis based on the CFD is performed again by using the obtained surface outflow velocity V as a velocity boundary condition of each node, and thus the pressure P of each node is obtained. In other words, the blood flow simulation unit 12 performs weak coupling analysis every second in which the pressure P obtained through the CFD is applied to each node of the blood vessel surface, and the surface outflow velocity V of each node is taken as a velocity boundary condition on the basis of the pressure P. Consequently, a blood flow in the blood vessel region B can be simulated.

Next, a description will be made of a method of calculating the line resistance SR applied to each node of the surface of the blood vessel region.

Figure 4:
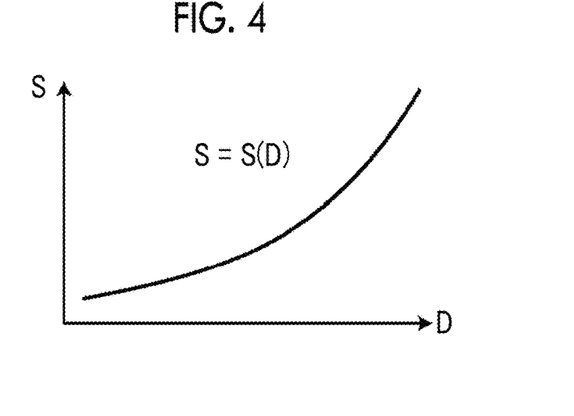
FIG. 4 is a diagram illustrating an example of a function indicating a relationship between a diameter of a blood vessel region and a surface area of a segment.

First, the segment is a partial section of the blood vessel in which the blood vessel region having the same diameter D is expected to run. A length (running distance) of the segment is acquired in advance on the basis of anatomical data. In a case where a diameter of the blood vessel region is indicated by D, a surface area S of the segment is calculated according to (S=πD×running distance). In other words, the surface area S may be represented as a function of the diameter D as illustrated in FIG. 4, and this function is set in advance. In a case where the line resistance SR of each node of the surface of the blood vessel region is calculated, the diameter D at a position of the node is acquired, and the surface area S of the segment for the node is obtained on the basis of the diameter D and the function illustrated in FIG. 4.

Figure 5:
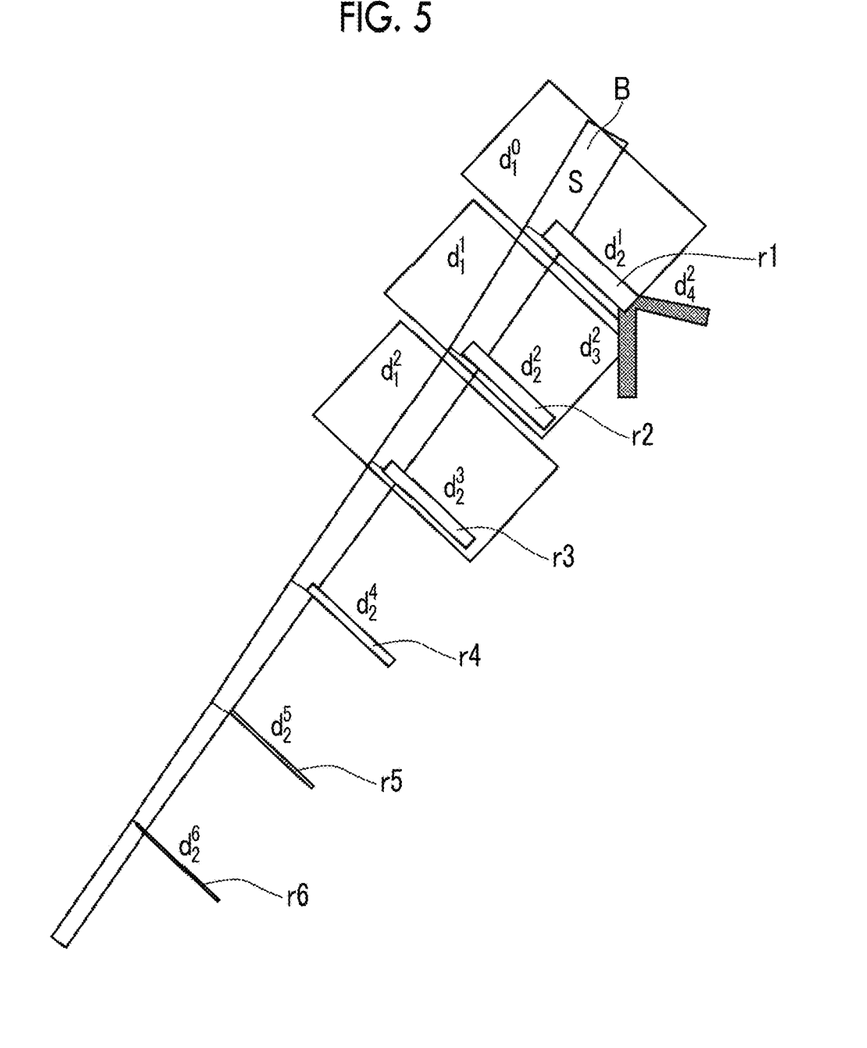
FIG. 5 is a schematic diagram for explaining a method of calculating a line resistance.

Next, a description will be made of a method of calculating the branch resistance R allocated to each node of the surface of the blood vessel region. The branch resistance R is a resistance value corresponding to a branch blood vessel which cannot be extracted from the three-dimensional medical image 6 as described above. Therefore, in the present embodiment, a peripheral vascular model corresponding to a branch blood vessel is generated for each node of the surface of the blood vessel region extracted from the three-dimensional medical image 6, and a combined resistance of the peripheral vascular model is used as the branch resistance R. Hereinafter, a description will be made of a method of generating a peripheral vascular model. FIG. 5 is a diagram for explaining a method of generating a peripheral vascular model. A thick linear region illustrated in FIG. 5 indicates the blood vessel region B extracted from the three-dimensional medical image 6, and regions r1 to r6 branching out of the blood vessel region B indicate peripheral vascular models. Rectangular shapes illustrated in FIG. 5 indicate segments. FIG. 5 illustrates only segments for predetermined nodes, but, actually, a segment is set for each node, and a peripheral vascular model is generated for each segment.

First, the diameter D of the blood vessel region B at a position of each node of the surface of the blood vessel region B is obtained. A branch index, a flow rate distribution ratio, and a major axis ratio of a peripheral vascular model (branch blood vessel) connected to each node are acquired on the basis of the diameter D at the position of each node. A branch index, a flow rate distribution ratio, and a major axis ratio corresponding to the diameter D of the blood vessel region B are set in advance according to a probability distribution based on anatomical data. A peripheral vascular model is generated as a fractal theory model in which two branches such as a Y shape are repeated with the beginning of a blood vessel directly connected to the blood vessel region B on the basis of the branch index, the flow rate distribution ratio, and the major axis ratio.

If a fluid resistance model in which a Hagen-Poiseuille flow is assumed is applied to the peripheral vascular model generated in the above-described way, a resistance value of a flow in a case where blood flows through the peripheral vascular model can be calculated. However, a parameter such as the branch index used to generate the peripheral vascular model has a variation according to a probability distribution. Therefore, a plurality of peripheral vascular models are generated by using a Monte Carlo method, a mean value or a median of the resistance values calculated for the plurality of peripheral vascular models is calculated, and the mean value or the median is used as the branch resistance R.

Figure 6:
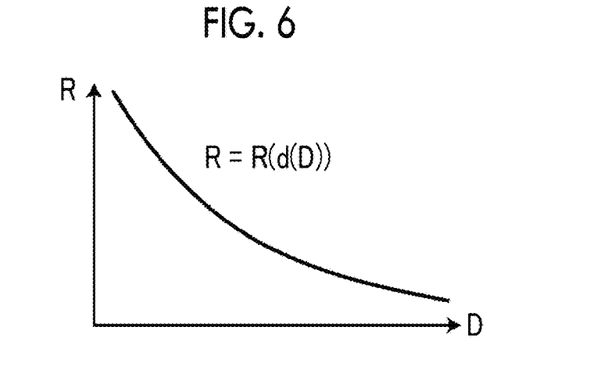
FIG. 6 is a diagram illustrating an example of a function indicating a relationship between a diameter of a blood vessel region and a branch resistance of a branch blood vessel.

As described above, a peripheral vascular model connected to each node is generated on the basis of the diameter D of the blood vessel region B at each node, and the branch resistance R is calculated on the basis of the generated peripheral vascular model. Therefore, the branch resistance R of each node may be represented as a function of the diameter D as illustrated in FIG. 6. Here, d(D) illustrated in FIG. 6 is a diameter of a branch blood vessel connected to a position with the diameter D, and a peripheral vascular model is generated on the basis of d(D). A relationship between the diameter D of the blood vessel region B and the diameter d(D) of the branch blood vessel is a relationship as illustrated in FIG. 7.

Figure 7:
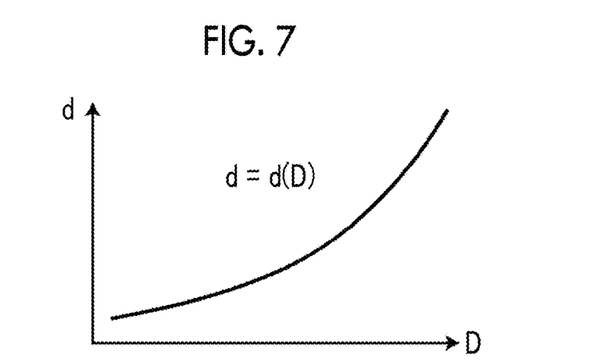
FIG. 7 is a diagram illustrating an example of a function indicating a relationship between a diameter of a blood vessel region and a diameter of a branch blood vessel.

In the above-described way, the branch resistance R of each node is calculated by using the functions illustrated in FIGS. 6 and 7 on the basis of the diameter D at a position of each node of the blood vessel region B. The surface area S set for each node is multiplied by the branch resistance R, and thus the line resistance SR is calculated.

Figure 8:
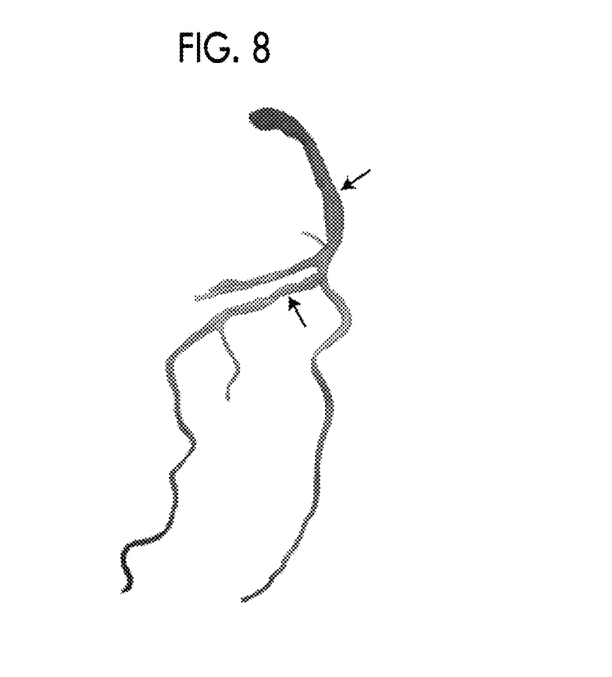
FIG. 8 is a diagram illustrating an example in which a blood flow simulation result is displayed to overlap the blood vessel region.

Referring to FIG. 1 again, the display control unit 13 displays a result of the blood flow simulation in the blood flow simulation unit 12 on the display unit 3. Regarding a method of displaying a blood flow simulation result, for example, an image indicating a blood flow may be generated and displayed on the basis of the blood flow simulation result. As an image indicating a blood flow, for example, as illustrated in FIG. 8, an image is generated in which a color corresponding to a blood flow velocity may be allocated to a blood vessel region extracted from the three-dimensional medical image 6, and this image may be displayed in colors so as to overlap the blood vessel region. A change in a blood flow velocity may be displayed in colors as a motion picture. As illustrated in FIG. 8, a stenotic part may be specified on the basis of the change in the blood flow velocity, and an image of an arrow indicating the stenotic part may be displayed. An image indicating a blood flow is not limited to color display as illustrated in FIG. 8, and a flow velocity vector indicating a blood flow direction may be displayed, and a flow line or a path line may be displayed.

The blood flow simulation unit 12 may specify a stenotic part on the basis of a blood flow simulation result, and measure an FFR in the stenotic part, and the display control unit 13 may display a measurement result of the FFR on the display unit 3. In a case where a measurement result of the FFR is displayed as mentioned above, a user may designate a measurement target location of the FFR by using the input unit 4 on the blood vessel region displayed on the display unit 3.

The medical image storage server 2 is a computer which preserves and manages various pieces of data, and includes a large capacity storage device and a database management program. The medical image storage server 2 acquires the three-dimensional medical image 6 captured in advance from an imaging device such as CT device via a network, and preserves the three-dimensional medical image 6 in the large capacity storage device and manages the three-dimensional medical image 6.

The input unit 4 receives various setting inputs from a user, and includes input devices such as a keyboard or a mouse. The input unit 4 receives, for example, a setting input of identification information of a patient and designation of a measurement target location of the FFR.

Figure 9:
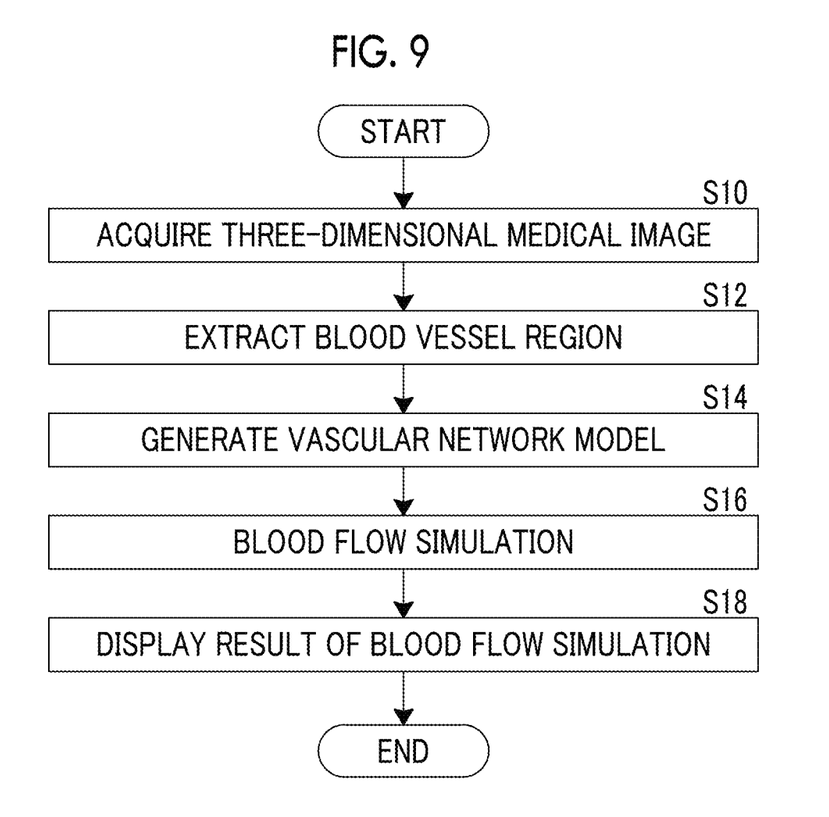
FIG. 9 is a flowchart for explaining an operation of the blood flow analysis system using the embodiment of the blood flow analysis device of the present invention.

Next, a description will be made of an operation of the blood flow analysis system of the present embodiment with reference to a flowchart illustrated in FIG. 9.

First, the three-dimensional medical image 6 of a patient is acquired by the three-dimensional image acquisition unit 10 in response to a setting input such as identification information of the patient from a user (S10). In the present embodiment, as described above, the three-dimensional medical image 6 of the heart is acquired.

The three-dimensional medical image 6 of the heart acquired by the three-dimensional image acquisition unit 10 is input to the blood vessel region extraction unit 11, and the blood vessel region extraction unit 11 extracts a blood vessel region from the input three-dimensional medical image 6 (S12).

The blood vessel region extracted by the blood vessel region extraction unit 11 is acquired by the blood flow simulation unit 12, and, as described above, the blood flow simulation unit 12 generates a vascular network model by applying the line resistance SR to each node of the surface of the blood vessel region in the above-described way (S14). The blood flow simulation unit 12 performs blood flow analysis through CFD by using the vascular network model, so as to perform blood flow simulation (S16).

A blood flow simulation result in the blood flow simulation unit 12 is output to the display control unit 13, and the display control unit 13 performs color display of the blood vessel region so as to display the blood flow simulation result (S18).

According to the blood flow analysis system of the embodiment, the line resistance SR is obtained by multiplying the branch resistance R corresponding to a branch blood vessel branching out of a blood vessel region and the surface area S of each of segments into which the blood vessel region is divided in an extension direction, a vascular network model is generated by applying the line resistance SR to each node of a surface of the blood vessel region, and blood flow simulation is performed by using the vascular network model. In other words, since the line resistance SR is calculated by taking into consideration a fine blood vessel of the fine artery level or less, and is applied to each node of the surface of the blood vessel region, blood flow simulation can be performed by using a vascular network model obtained by modeling even the fine blood vessel of the fine artery level or less. Consequently, a blood flow flowing through a blood vessel can be analyzed with high accuracy, and thus an FFR or the like can be measured with high accuracy.

Figure 10:
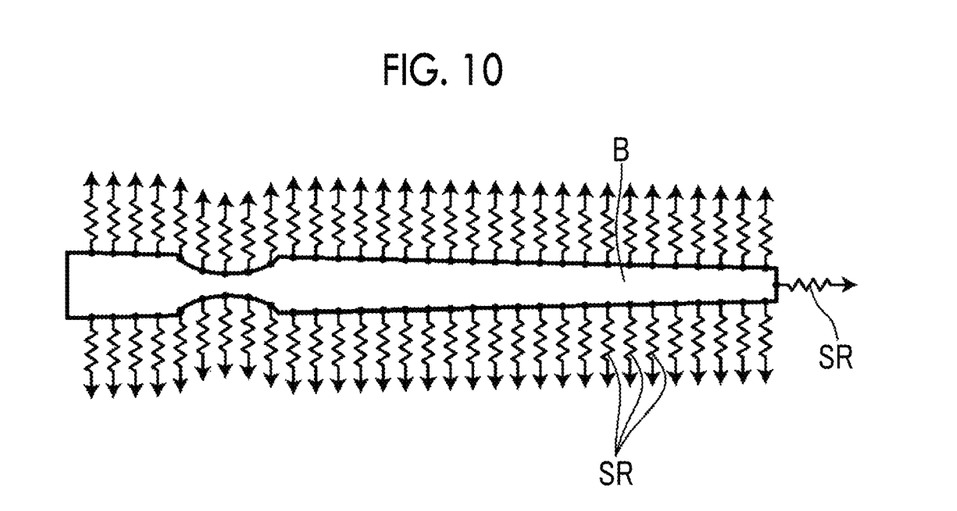
FIG. 10 is a diagram illustrating an example of a vascular network model in which a line resistance calculated on the basis of a peripheral vascular model is applied to an end of the blood vessel region.

In the description of the embodiment, a peripheral vascular model is generated for each node of the blood vessel region extracted from the three-dimensional medical image 6, but a peripheral vascular model may also be connected to an end of the blood vessel region. As illustrated in FIG. 10, a vascular network model may be generated by applying the line resistance SR calculated on the basis of a peripheral vascular model, to the end of the blood vessel region.

In the embodiment, a peripheral vascular model is generated on the basis of a diameter of the blood vessel region at a position of each node of the surface of the blood vessel region, and a combined resistance of the peripheral vascular models is set as the branch resistance R, that is, the branch resistance R is changed depending on the diameter of the blood vessel region, but the branch resistance R may be changed depending on not only the diameter of the blood vessel region but also a sectional area or a volume per length of the blood vessel region at a position of each node. A "size of a blood vessel region" in the present invention is assumed to include not only a diameter of the blood vessel region but also a sectional area or a volume per length.

The surface area S of a segment of each node is calculated on the basis of a diameter of a blood vessel region at a position of each node of a surface of the blood vessel region, that is, the surface area S of the segment is changed depending on the diameter of the blood vessel region, but the surface area S of the segment may be changed depending on not only the diameter of the blood vessel region but also a sectional area or a volume per length of the blood vessel region at a position of each node.

In the embodiment, a velocity boundary condition of a blood vessel surface is obtained through weak coupling analysis, but is not limited thereto, and the velocity boundary condition may be obtained through strong coupling analysis in which a line resistance is solved by being incorporated into a single equation.

Regarding a resistance value corresponding to a branch blood vessel, as illustrated in FIG. 2, only a resistive element component may be set by taking into consideration only viscous resistance, and an inductor component may be connected in series to a resistive element component by also taking into consideration viscous resistance. Consequently, outflow from a blood vessel region surface can be primarily delayed such that a rapid change can be suppressed, and thus it is possible to improve stability of simulation.

A solution is not limited to the method of the embodiment, and, for example, a porous model of a cardiac muscle may be generated, and a line resistance may be replaced with a permeability coefficient such that the porous model of the cardiac muscle is solved.

What is claimed is:

1. A blood flow analysis device comprising:
   a memory configured to store instructions; and
   a processor configured to execute the stored instructions, which comprise:
   extracting a blood vessel region from a three-dimensional medical image of a subject including a blood vessel;
   generating a vascular network model by setting nodes on a surface of the extracted blood vessel region and applying a line resistance corresponding to a diameter of the extracted blood vessel region at each position of the nodes to each of the nodes; and
   performing simulation of a blood flow by using the vascular network model,
   wherein the line resistance corresponding to the diameter is obtained by using a function obtained based on anatomical data in advance, the line resistance being a value obtained by multiplying a resistance value corresponding to a branch blood vessel assumed to branch out of a section of the blood vessel region having the diameter by a surface area which the section is assumed to have.

2. The blood flow analysis device according to claim 1, wherein the processor is further configured to execute the stored instructions which changes the resistance value corresponding to the branch blood vessel according to a size of the blood vessel region in which each node is disposed.

3. The blood flow analysis device according to claim 1, wherein the processor is further configured to execute the stored instructions which changes the surface area according to a size of the blood vessel region in which each node is disposed.

4. The blood flow analysis device according to claim 1, wherein the processor is further configured to execute the stored instructions which connects a peripheral vascular model which does not appear as the blood vessel region on the three-dimensional medical image to an end of the blood vessel region, and applies a line resistance calculated on the basis of the peripheral vascular model to the end of the blood vessel region, so as to generate the vascular network model.

5. The blood flow analysis device according to claim 1, wherein the processor is further configured to execute the stored instructions which extracts the blood vessel region including coronary artery from the three-dimensional medical image of a heart as the subject.

6. The blood flow analysis device according to claim 1, further comprising:
a display controller that displays an image indicating the blood flow on a display on the basis of a simulation result of the blood flow.

7. The blood flow analysis device according to claim 6, wherein the display controller displays the image indicating the blood flow to overlap the blood vessel region.

8. The blood flow analysis device according to claim 6 wherein the display controller displays the image indicating the blood flow in colors.

9. The blood flow analysis device according to claim 7, wherein the display controller displays the image indicating the blood flow in colors.

10. A blood flow analysis method comprising:
extracting a blood vessel region from a three-dimensional medical image of a subject including a blood vessel;
generating a vascular network model by setting nodes on a surface of the extracted blood vessel region and applying a line resistance corresponding to a diameter of the extracted blood vessel region at each position of the nodes to each of the nodes and
performing simulation of a blood flow by using the vascular network model,
wherein the line resistance corresponding to the diameter is obtained by using a function obtained based on anatomical data in advance, the line resistance being a value obtained by multiplying a resistance value corresponding to a branch blood vessel assumed to branch out of a section of the blood vessel region having the diameter by a surface area which the section is assumed to have.

11. A non-transitory computer-readable storage medium storing therein a blood flow analysis program causing a computer to:
extract a blood vessel region from a three-dimensional medical image of a subject including a blood vessel;
generate a vascular network model by setting nodes on a surface of the extracted blood vessel region and applying a line resistance corresponding to a diameter of the extracted blood vessel region at each position of the nodes to each of the nodes and
perform simulation of a blood flow by using the vascular network model,
wherein the line resistance corresponding to the diameter is obtained by using a function obtained based on anatomical data in advance, the line resistance being a value obtained by multiplying a resistance value corresponding to a branch blood vessel assumed to branch out of a section of the blood vessel region having the diameter by a surface area which the section is assumed to have.

* * * * *